(12) United States Patent
Tsai et al.

(10) Patent No.: US 9,541,500 B2
(45) Date of Patent: Jan. 10, 2017

(54) METHOD FOR CALIBRATING A MANUFACTURING PROCESS MODEL

(75) Inventors: Kuen-Yu Tsai, Taipei (TW); Alek Chi-Heng Chen, New Taipei (TW); Jia-Han Li, Taipei (TW)

(73) Assignees: ASML Netherlands B.V., Veldhoven (NL); National Taiwan University, Taipei (TW)

( * ) Notice: Subject to any disclaimer, the term of this patent is extended or adjusted under 35 U.S.C. 154(b) by 924 days.

(21) Appl. No.: 13/599,385

(22) Filed: Aug. 30, 2012

(65) Prior Publication Data

US 2013/0073070 A1    Mar. 21, 2013

Related U.S. Application Data

(60) Provisional application No. 61/537,248, filed on Sep. 21, 2011.

(51) Int. Cl.
*G06F 17/50* (2006.01)
*G01N 21/47* (2006.01)
*G01N 21/956* (2006.01)

(52) U.S. Cl.
CPC ............ *G01N 21/47* (2013.01); *G01N 21/956* (2013.01)

(58) Field of Classification Search
CPC ............................... G01N 21/47; G01N 21/956
(Continued)

(56) References Cited

U.S. PATENT DOCUMENTS 7,089,075 B2 * 8/2006 Hasan .................... G05B 15/02
                                                                    700/109
7,175,940 B2 * 2/2007 Laidig et al. .................... 430/5
(Continued)

FOREIGN PATENT DOCUMENTS

KR    10-2008-0061588 A    7/2008

OTHER PUBLICATIONS

English-Language Abstract for Korean Patent Publication No. 10-2008-0061588 A, published Jul. 3, 2008; 1 page.
(Continued)

*Primary Examiner* — Jack Chiang
*Assistant Examiner* — Brandon Bowers
(74) *Attorney, Agent, or Firm* — Sterne, Kessler, Goldstein & Fox P.L.L.C.

(57) ABSTRACT

Calibration of models for manufacturing processes that are subject to circuit layout proximity effects is performed, including optical proximity correction (OPC) model calibration. A target structure is produced using a layout and a manufacturing process. The target structure is illuminated and an electromagnetic scattering property is detected. A manufacturing process model for simulation of the manufacturing process is produced, which comprises at least one manufacturing process parameter determining a model electromagnetic scattering property using the manufacturing process model and the layout. The model electromagnetic scattering property is compared to the detected electromagnetic scattering property and based on the result of the comparison, calibrated manufacturing process parameters are output for calibrating the manufacturing process model. The determining and the layout may include determining structural information corresponding to the target structure using the manufacturing process model and determining the model electromagnetic scattering property using the structural information.

14 Claims, 4 Drawing Sheets

(58) Field of Classification Search
USPC .................................................. 716/52–54
See application file for complete search history.

(56) References Cited

U.S. PATENT DOCUMENTS

| | | | |
|---|---|---|---|
| 7,566,517 | B1 | 7/2009 | Adel et al. |
| 7,589,832 | B2 * | 9/2009 | Den Boef .......... G01N 21/4788 |
| | | | 356/237.2 |
| 7,700,247 | B2 * | 4/2010 | Ausschnitt ...................... 430/30 |
| 2006/0266243 | A1 | 11/2006 | Percin et al. |
| 2008/0304029 | A1 | 12/2008 | Pforr et al. |
| 2009/0172616 | A1 | 7/2009 | Lapanik |
| 2010/0280812 | A1 * | 11/2010 | Zhang ............................ 703/13 |

OTHER PUBLICATIONS

Charley, A.-L., et al., "Line-end gap measurement with YieldStar scatterometer: towards an OPC model calibration," Proceedings of SPIE Metrology, Inspection, and Process Control for Microlithography XXVI, vol. 8324, 2012; pp. 83242I-1 to 83242I-8.

Chen, C.-Y., et al., "Direct-scatterometry-enabled lithography model calibration," Proceedings of SPIE, Metrology, Inspectiom, and Process Control for Microlithography XXVI, vol. 8324, 2012; pp. 83241R-1 to 83241R-12.

Dave, A.D., et al., "Calibrating OPC model with full CD profile data for 2D and 3D patterns using scatterometry," Proceedings of SPIE, Optical Microlithography, XXII, vol. 7274, 2009; pp. 727415-1 to 727415-9.

Villarrubia, J.S., et al., "Scanning electron microscope analog of scatterometry," Metrology, Inspection, and Process Control for Microlithography, Proceedings of SPIE, vol. 4689, 2002; pp. 304-312.

* cited by examiner

METHOD FOR CALIBRATING A MANUFACTURING PROCESS MODEL

CROSS REFERENCE TO RELATED APPLICATIONS

This application claims the benefit under 35 U.S.C. §119(e) to U.S. Provisional Patent Application No. 61/537,248, filed Sep. 21, 2011, which is incorporated by reference herein in its entirety.

FIELD

The present invention relates to methods for calibrating manufacturing process models, for example process proximity effect models including optical proximity effects for optical proximity correction (OPC), usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Optical lithography processes cannot reproduce patterns faithfully independent of the proximity to their neighbors. As a result, complex manufacturing process models including optical proximity effects to provide optical proximity correction (OPC) are used to compensate for this effect. An accurate manufacturing model needs to have its behavior calibrated to the resulting pattern on the wafer. Typically, in such calibration features on the wafer are measured using a CD (Critical Dimension) SEM (Scanning Electron Microscope) metrology tool. This type of tools has limitations in measuring 2-D (2-Dimensional) structures, especially in determination of the separation of ends of fine features (or line ends). As a result, the manufacturing model's accuracy is limited by the uncertainty of the measurement accuracy of the wafer feature metrology tool. In CD SEM measurement results, there is also a lack of information on resist side wall profiles.

The scatterometry technique is known for its improvement in measurement precision versus that of the CD SEM. However, the scatterometry technique has problem measuring arbitrary 2-D patterns. It also has many difficulties in achieving a robust CD reconstruction algorithm.

SUMMARY

It would be desirable to calibrate a manufacturing process model such as one modelling optical proximity effects while benefitting from the advantage of the measurement precision of scatterometry but without having to perform CD reconstruction.

According to an aspect of the present invention, there is provided a method of calibrating a manufacturing process model, the method including the steps providing a layout for a target structure, producing a target structure using the layout and a manufacturing process, illuminating the target structure and detecting an electromagnetic scattering property arising from the illumination, providing a manufacturing process model for simulation of the manufacturing process, the manufacturing process model comprising at least one manufacturing process parameter, determining a model electromagnetic scattering property using the manufacturing process model and the layout, comparing the model electromagnetic scattering property to the detected electromagnetic scattering property, and based on the result of the comparison, outputting calibrated manufacturing process parameters for calibrating the manufacturing process model.

According to a second aspect of the present invention, there is provided a computer program product containing one or more sequences of machine-readable instructions for calibrating a manufacturing process model, the instructions being adapted to cause one or more processors to perform a method including the steps receiving a layout for a target structure, receiving a detected electromagnetic scattering property arising from illumination of a target structure produced using the layout and a manufacturing process, executing a manufacturing process model to simulate the manufacturing process, the manufacturing process model comprising at least one manufacturing process parameter, determining a model electromagnetic scattering property using the manufacturing process model and the layout, comparing the model electromagnetic scattering property to the detected electromagnetic scattering property, and based on the result of the comparison, outputting calibrated manufacturing process parameters for calibrating the manufacturing process model.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
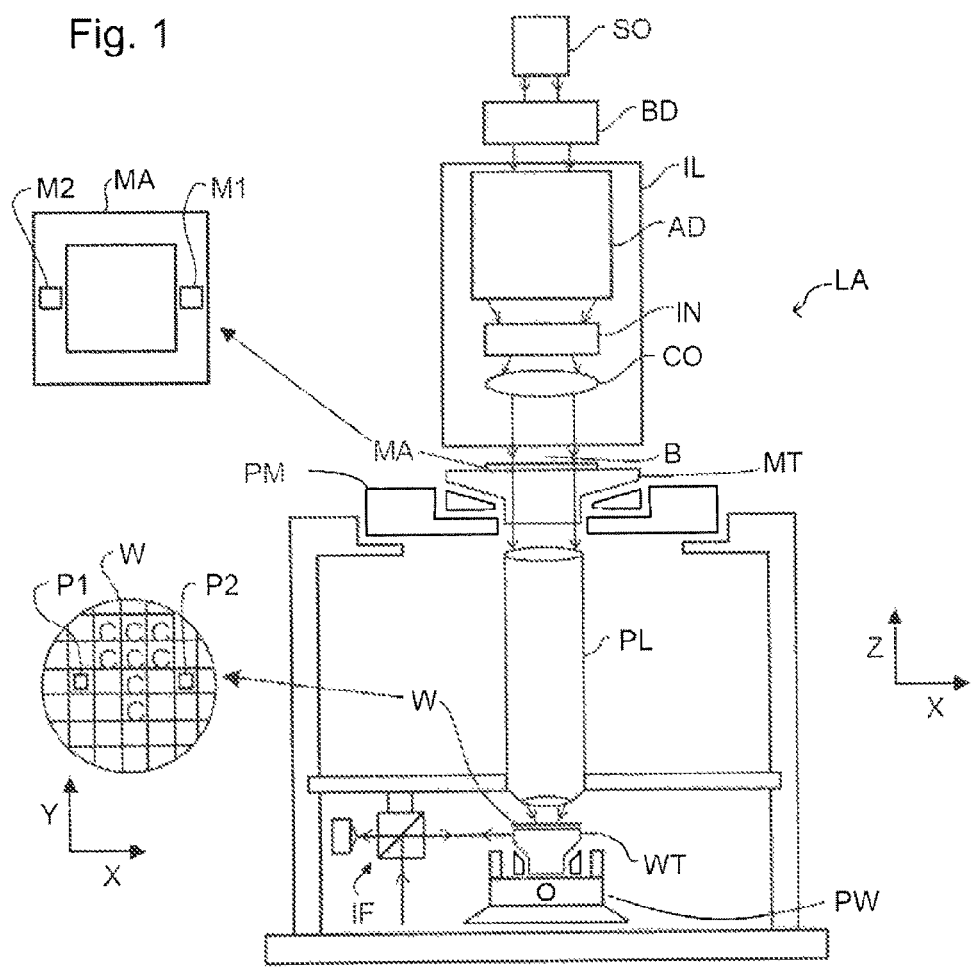
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
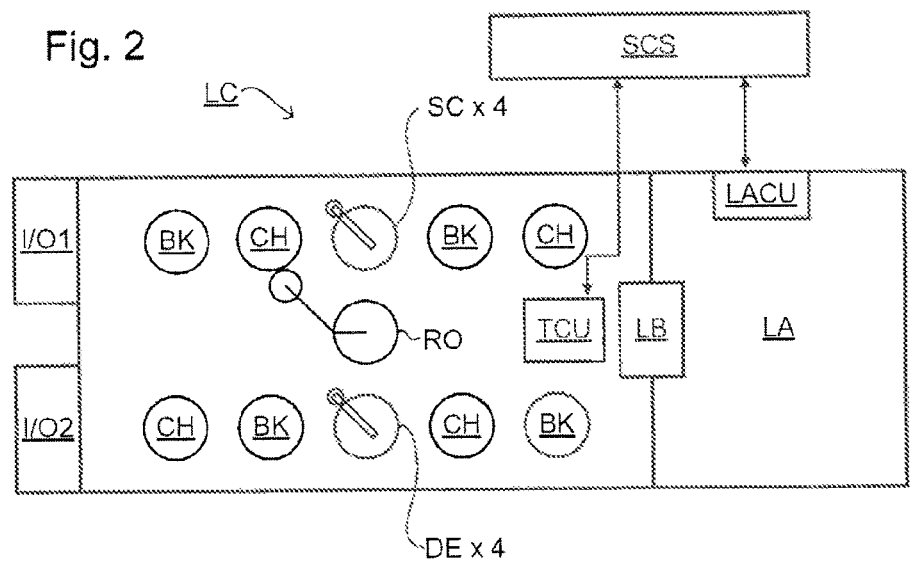
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
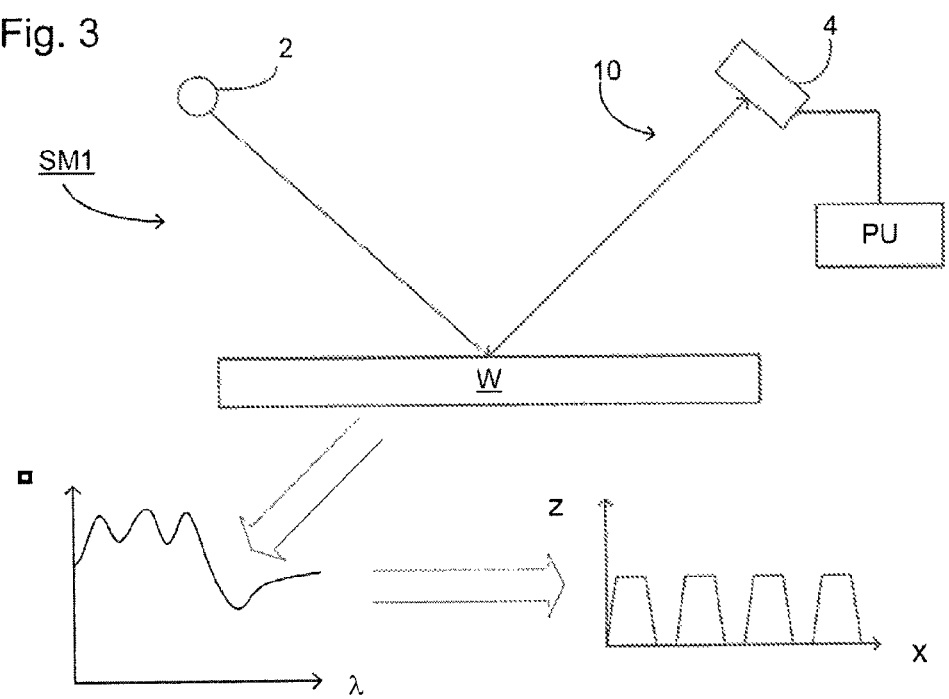
FIG. 3 depicts a first scatterometer.

FIG. 3 depicts a known scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
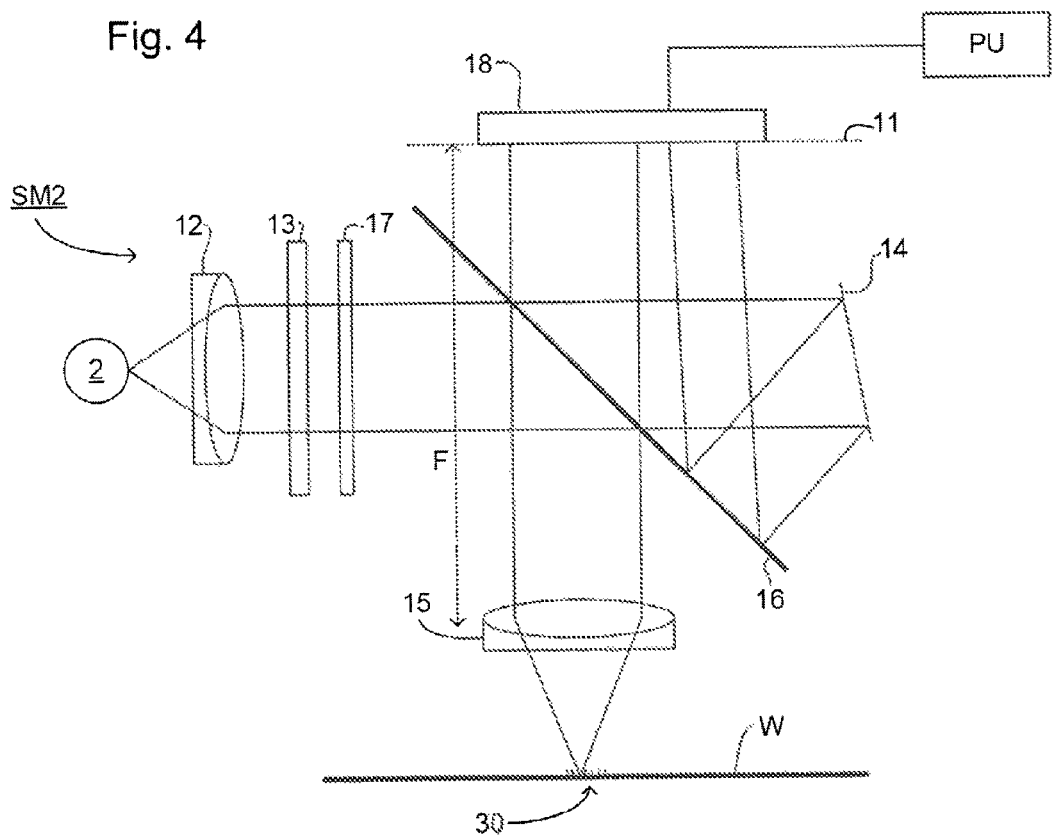
FIG. 4 depicts a second scatterometer.

Another scatterometer that may be used with an embodiment of the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the target can be performed in a number of ways. In a first type of process, represented by FIG. 5, a diffraction pattern based on a first estimate of the target structure (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
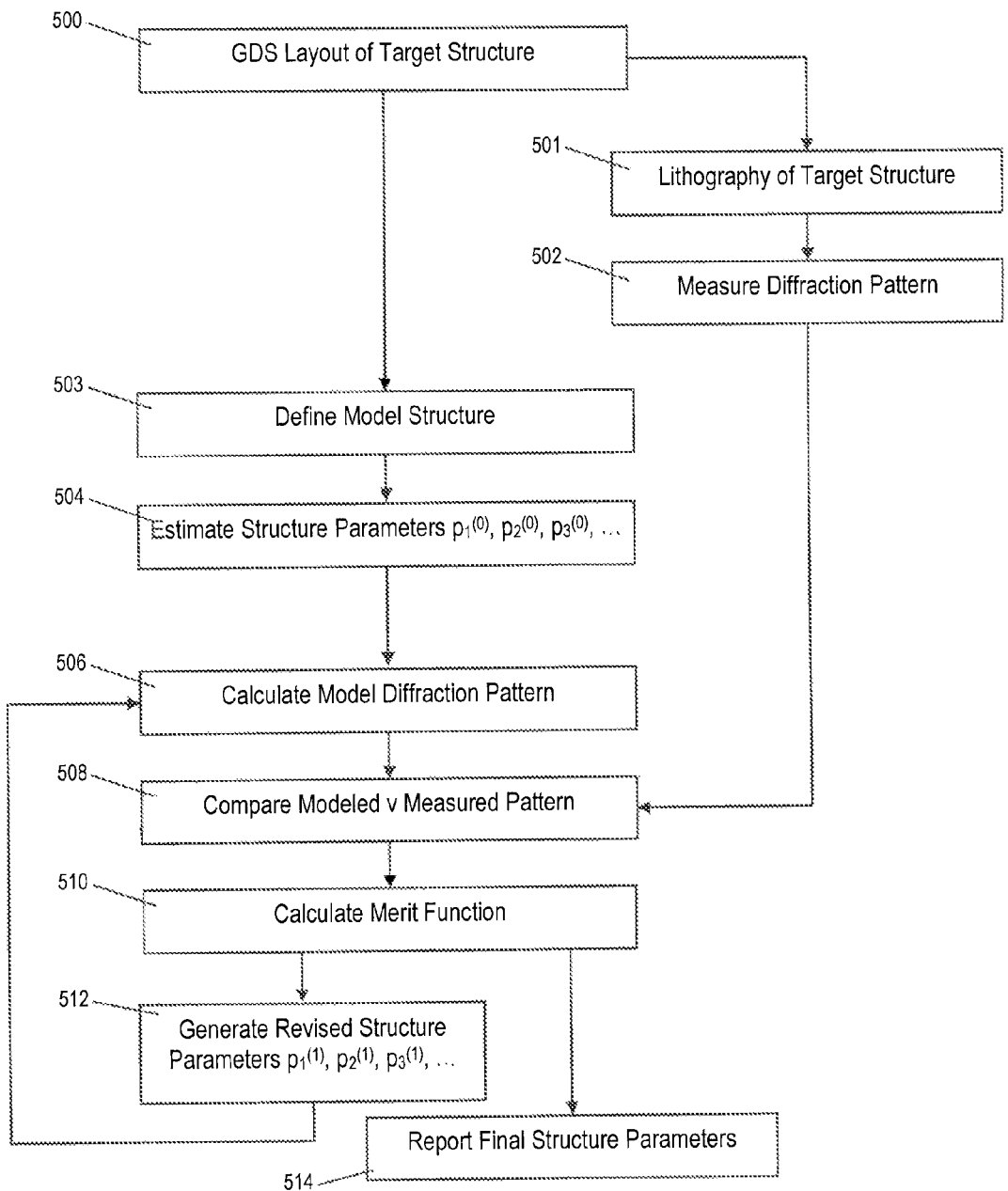
FIG. 5 depicts an example process for reconstruction of a structure from scatterometer measurements.

Referring to FIG. 5 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 500: A layout defining the structure of the target structure is provided, for example in the standard GDS file format.

In step 501: The layout is used to produce the target structure on the substrate, for example using the lithographic apparatus and cell described with reference to FIGS. 1 and 2.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$.

In step 504: A model target structure is estimated by setting initial values $p_i^{(0)}$ for the floating parameters (i.e. $p_1^{(0)}$, $p_2^{(0)}$, $p_3^{(0)}$ and so on). Each floating parameter will be generated within certain predetermined ranges, as defined in the recipe.

In step 506: The parameters representing the estimated target structure, including shape together with the optical properties of the different elements of the model, are used to calculate the scattering properties, for example using a rigorous optical diffraction method such as RCWA or any other solver of Maxwell equations. This gives an estimated or model diffraction pattern of the estimated target structure.

In steps 508, 510: The measured diffraction pattern and the model diffraction pattern are then compared and their similarities and differences are used to calculate a "merit function" for the model target structure.

In step 512: Assuming that the merit function indicates that the model needs to be improved before it represents accurately the actual target structure, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e., the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Embodiments of the present invention may be used to calibrate models for manufacturing processes subject to circuit layout proximity effects. This includes OPC model calibration. The calibration can be performed using scatterometry, for example using a scatterometry CD (SCD) tool.

Figure 6:
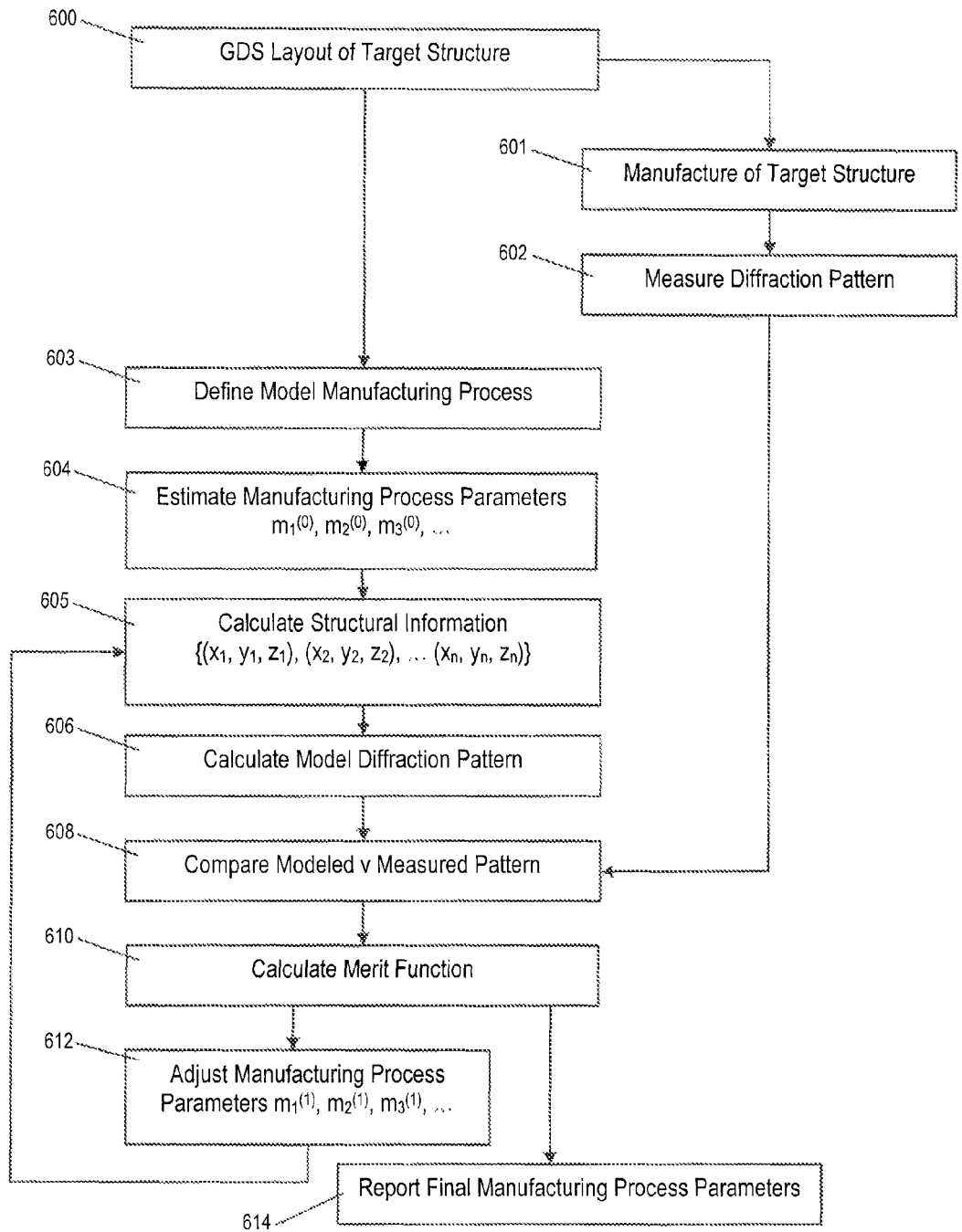
FIG. 6 depicts a method of calibrating a manufacturing process model in accordance with an embodiment of the present invention.

Referring to FIG. 6, a method of calibrating manufacturing process parameters in a manufacturing process model, according to an embodiment of the present invention, is shown in detail.

In step 600: A layout defining the structure of the test target structure is provided, for example in the standard GDS file format. The layout may for example include a set of polygons, with Manhattan or non-Manhattan geometry and/or standard cell layouts for integrated circuits to be manufactured using a manufacturing process. To ease the adoption of using scatterometry for OPC model calibration, a set of more regular 2D patterns can be used to have adequate imaging pupil coverage in the lithography apparatus. Furthermore, the additional side wall profile information in the scattered signal can be used to predict the final feature size after pattern transfer via an etching process.

In step 601: The layout is used to produce the target structure on the substrate, for example using a lithographic manufacturing process performed with the lithographic apparatus and cell described with reference to FIGS. 1 and 2. The manufacturing process may include other processing steps, including for example etching.

In step 602: The target structure is illuminated and an electromagnetic scattering property arising from the illumination is detected. In this embodiment, the diffraction pattern of the actual target on the substrate is measured using a scatterometer such as those described above with reference to FIG. 3 or 4. This measured diffraction pattern is forwarded to a calculation system such as a computer. The calculation system may be the processing unit PU referred to above, or it may be a separate apparatus.

In step 603: A manufacturing process model for simulation of the manufacturing process is provided. In this embodiment, the manufacturing process model includes the optical proximity effect. The proximity effect can be corrected, for example by adjusting the reticle features or adding structures such as sub-resolution assisted features (SRAF) to compensate for the effect, known as optical proximity correction (OPC). The parameterized model of the manufacturing process is defined in terms of a number of manufacturing process parameters $m_i$ ($m_1$, $m_2$, $m_3$ and so on). While the manufacturing process may be defined by dozens of parameters, the manufacturing process model will define many of these to have fixed values, while others are to be variable or 'floating' parameters for the purpose of the following process steps. For the purposes of describing FIG. 6, only the variable parameters are considered as parameters $m_i$.

In step 604: A model manufacturing process is estimated by setting initial values $m_i^{(0)}$ for the floating manufacturing process parameters (i.e., $m_1^{(0)}$, $m_2^{(0)}$, $m_3^{(0)}$ and so on). Each floating parameter will be generated within certain predetermined ranges.

In the subsequent steps 605 and 606, described below, a model electromagnetic scattering property, in this embodiment a model diffraction pattern, is determined using the manufacturing process model to produce structural information.

In step 605: The manufacturing process model is executed to produce a model target structure by calculating structural information $(x_i^{(0)}, y_i^{(0)}, z_i^{(0)})$ (i.e., $\{(x_1^{(0)}, y_1^{(0)}, z_1^{(0)}), (x_2^{(0)}, y_2^{(0)}, z_2^{(0)}), \ldots (x_n^{(0)}, y_n^{(0)}, z_n^{(0)})\}$) relating to the target structure.

An advantage of embodiments of the present invention is the capability of using arbitrary geometry description for the developed resist profile as long as the subsequent optical scattering simulation can be performed. The resist profile can have a very complicated 3-D surface for which the line width (CD), line length, and profile angle cannot accurately parameterized. A more accurate set of parameters is the set of 3-D coordinates $\{(x_1^{(0)}, y_1^{(0)}, z_1^{(0)}), (x_2^{(0)}, y_2^{(0)}, z_2^{(0)}), \ldots (x_n^{(0)}, y_n^{(0)}, z_n^{(0)})\}$, which may be approximated by a set of functions for directly representing the 3-D surface.

The structural information may be a 3-D description of the target structure (or 3-D surface). The structural information may for example comprise: (i) a 3-D coordinate system description; (ii) an approximation of a set of surface functions; or (iii) 2-D contours of structure (top-down) plus side-wall angle (or equivalent) to approximate the third dimension. For example, consider the case of a resist line (with the x,y dimensions describing the contour and z dimension showing height) with surface roughness along the wall of the resist in x-z and y-z planes. This resist line can be described by a 3-D coordinate system to simulate the scattered signal. Or this resist line can be approximated by a smoothing algorithm, to eliminate the high frequency surface roughness, so that the resist line can be described a surface function or functions. Another approximation is to reduce this structure to a line-width, height and side-wall angle.

In step 606: The structural information representing the model target structure, which may include shape together with the optical properties of the different elements of the model, are used to calculate the model scattering properties, for example using a rigorous optical diffraction method such as RCWA or any other solver of Maxwell equations. Thus an estimated or model diffraction pattern of the estimated target structure is determined using the structural information resulting from the manufacturing process model.

In steps 608, 610: The measured diffraction pattern and the model diffraction pattern are then compared and their similarities and differences are used to calculate a "merit function" or comparison value for the modeled target structure. In the remaining steps, the manufacturing process model is calibrated based on the result of this comparison.

In step 612: If the merit function indicates that the manufacturing process model needs to be improved before it reproduces accurately the measured scattering properties, new manufacturing process parameters $m_1^{(1)}$, $m_2^{(1)}$, $m_3^{(1)}$, etc. are estimated (thus the parameters are adjusted based on the result of the comparison in step 608) and fed back iteratively into step 605. Steps 605-610 are repeated, using the adjusted parameters, with step 612 also repeated as many times as necessary. Mathematical optimization may be used to change the manufacturing process parameters.

In order to assist the search, the calculations in step 604 to 606 may further generate partial derivatives of the merit function, indicating the sensitivity with which increasing or decreasing a manufacturing process parameter will increase or decrease the merit function, in this particular region in the parameter space. The calculation of merit functions and the use of derivatives is generally known in the art, and will not be described here in detail.

In step 614: When the merit function indicates that this iterative process has converged on a solution with a desired accuracy, for example when the merit function meets a target value, the iteration is halted and the currently estimated manufacturing process parameters are reported as the calibrated parameters for the manufacturing process model.

The estimated or model diffraction pattern calculated at 606 can be expressed in various forms. Comparisons are simplified if the calculated pattern is expressed in the same form as the measured pattern generated in step 602. For example, a modeled spectrum can be compared easily with a spectrum measured by the apparatus of FIG. 3; a modeled pupil pattern can be compared easily with a pupil pattern measured by the apparatus of FIG. 4.

Scatterometry CD (SCD) can improve metrology uncertainty of regular patterns. However, it has problems measuring arbitrary 2-D patterns using CD reconstruction. Since angularly resolved scatterometers have the capability of capturing the imaging pupil of the target, a method of OPC model calibration using directly scattered signals, via scatterometer pupil data, without CD reconstruction, is disclosed. This has the benefit of avoiding the difficulty of reliably performing CD reconstruction on arbitrary 2D structures using conventional scatterometry techniques. Embodiments of the present invention utilize dense scattering detector signals directly, rather than utilizing sparse CD reconstruction results. Thus all the scattering information is used in calibration, which gives an accuracy advantage compared to using the sparse CD results. Both periodic and generic circuit targets may be used as calibration target structures in embodiments of the present invention.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of calibrating a manufacturing process model comprising:
    measuring, using a scatterometer, a diffraction pattern generated by illuminating a target structure, the target structure having been produced by a layout for the target structure and a manufacturing process;
    providing a manufacturing process model for simulation of the manufacturing process, the manufacturing process model comprising manufacturing process parameters;

determining structural information corresponding to the target structure using the manufacturing process model;

determining a model diffraction pattern using the structural information;

comparing the model diffraction pattern to the measured diffraction pattern and calculating a merit function based on a result of the comparison;

generating calibrated manufacturing process parameters based on a result of the merit function; and calibrating the manufacturing process model using the generated calibrated manufacturing process parameters.

2. The method of claim 1, wherein the structural information comprises 3-D description of the target structure.

3. The method of claim 1, wherein the generating comprises estimating at least one of the manufacturing process parameters.

4. The method of claim 3, further comprising, based on the result of the merit function, adjusting the at least one estimated manufacturing process parameter and repeating the determining and comparing using the adjusted at least one estimated manufacturing process parameter.

5. The method of claim 1, wherein the manufacturing process model models a lithographic process.

6. The method of claim 5, wherein the manufacturing process model comprises optical proximity correction.

7. The method of claim 1, wherein the manufacturing process model models an etching process.

8. The method of claim 1, wherein the diffraction pattern comprises an angularly resolved diffraction pattern.

9. A computer program product containing one or more sequences of machine-readable instructions for calibrating a manufacturing process model, the instructions being adapted to cause one or more processors to perform an operation comprising:

receiving a measured diffraction pattern of a target structure arising from an illumination of the target structure, the target structure having been produced based on a layout for the target structure and a manufacturing process;

executing a manufacturing process model to simulate the manufacturing process, the manufacturing process model comprising manufacturing process parameters;

determining structural information corresponding to the target structure using the manufacturing process model;

determining a model diffraction pattern using the structural information;

comparing the model diffraction pattern to the measured diffraction pattern and calculating a merit function based on a result of the comparison;

generating calibrated manufacturing process parameters based on a result of the merit function; and calibrating the manufacturing process model using the generated calibrated manufacturing process parameters.

10. A method of calibrating a structure model comprising:

measuring, using a scatterometer, a diffraction pattern generated by illuminating a target structure, the target structure being based on a layout;

simulating the target structure with a structure model, the structure model comprising a 3-D description of the target structure;

determining a model diffraction pattern using the structure model and the layout;

comparing the model diffraction pattern to the measured diffraction pattern to generate a comparison result; and generating calibrated 3-D description of the target structure based on the comparison result; and calibrating the structure model using the generated calibrated 3-D description.

11. The method of claim 10, wherein the comparing further comprises calculating a merit function based on a result of the comparison.

12. The method of claim 10, wherein the 3-D description of the target structure comprises a 3-D coordinate system description.

13. The method of claim 10, wherein the 3-D description of the target structure comprises an approximation of a set of surface functions.

14. The method of claim 10, wherein the 3-D description of the target structure comprises 2-D contours and side-wall angles of the target structure for estimating a third dimension value.

* * * * *